(12) United States Patent
Legrand et al.

(10) Patent No.: US 6,242,005 B1
(45) Date of Patent: Jun. 5, 2001

(54) ABSORBABLE PROPHYLACTIC COMPOSITION FOR PROTECTION AGAINST IONIZING OR NON-IONIZING ELECTROMAGNETIC WAVES

(76) Inventors: Charles Legrand, 14, Avenue de oreully F-14000; Rachid Bouhamidi, Le Clos Soli, Fue du Lavoir F-14440, both of Caen (FR)

( * ) Notice: Subject to any disclaimer, the term of this patent is extended or adjusted under 35 U.S.C. 154(b) by 0 days.

(21) Appl. No.: 09/051,507

(22) PCT Filed: Oct. 10, 1996

(86) PCT No.: PCT/FR96/01577

§ 371 Date: Sep. 28, 1998

§ 102(e) Date: Sep. 28, 1998

(87) PCT Pub. No.: WO97/13521

PCT Pub. Date: Apr. 17, 1997

(30) Foreign Application Priority Data

Oct. 13, 1995 (FR) .................................. 95 12034
Oct. 8, 1996 (FR) .................................. 95 12247

(51) Int. Cl.$^7$ ........................... A61K 9/14; A61K 35/78; A01N 65/00
(52) U.S. Cl. ........................................ 424/489; 424/195.1
(58) Field of Search .................. 424/195.1, 401, 424/59, 489

(56) References Cited

FOREIGN PATENT DOCUMENTS

| | | |
|---|---|---|
| 7092743 | 6/1970 | (FR) . |
| 7734555 | 11/1977 | (FR) . |
| 1 541 469 | * 2/1979 | (GB) . |
| 93/24106 | * 2/1979 | (WO) . |

OTHER PUBLICATIONS

XP 000 576292 1972 France—Article by Michael Flanzy.
XP 002008367 1992 Database WPI Week 9229.
Arts et al., Optimization of a quantitative method for the determination of catechins in fruits and legumes, Journal of Agricultural and Food Chemistry, vol. 46, No. 12, pp. 5156–62, Dec. 1998.*
Bombardelli et al., Vitis vinifera L., Fitoterapia, 66, No. 4, 291–317, 1995.*

* cited by examiner

*Primary Examiner*—Thurman K. Page
*Assistant Examiner*—Brian K. Seidleck
(74) *Attorney, Agent, or Firm*—Robert B. Hughes; Hughes & Schacht, PLLC

(57) ABSTRACT

An absorbable prophylactic composition for protecting against ionizing or nonionizing electromagnetic waves. The composition is derived from a crude extract of residual fractions of crushed grapes, and primarily from solid material comprising pips, stalks and skins of grapes and/or combinations thereof. The crude extract is obtained by first pulverizing the fraction or fractions from the grapes to form a powder, and then subjecting the powder to at least two extraction processes, one with acetone and the other with ethyl acetate. The extract is then ingested in doses between about 20 mg to 3 g for an adult male. Tests have demonstrated the efficacy of this composition against changes induced by ionizing radiation (x-rays) and nonionizing radiation (UV-C).

19 Claims, No Drawings

ABSORBABLE PROPHYLACTIC COMPOSITION FOR PROTECTION AGAINST IONIZING OR NON-IONIZING ELECTROMAGNETIC WAVES

This application is a 371 of PCT/FR96/01577, filed Oct. 10, 1996.

The present invention concerns the use of residual fractions of crushed grapes for preparing an absorbable prophylactic composition providing protection against ionising or non-ionising electromagnetic waves.

The production of free radicals and, in particular, of oxygenated free radicals is a normal physiological process at the cellular level not normally having deleterious consequences since the human organism is provided with protective systems: these protective systems are constituted either by enzymatic systems that trap oxygenated free radicals, such as SOD, or capable of decomposing secondary toxic products ($H_2O_2$) such as catalase, or by non-enzymatic systems such as vitamin E or glutathione.

It may happen, however, that the level of production of the oxygenated free radicals exceeds the capacities of the protective systems and they react with other molecules of the living cells, the consequences of which may be profound disturbances of the membranal integrity, the inactivation of many enzymatic systems, and profound modifications to the structure of the nucleic acids.

This hyper-production of oxygenated free radicals may result :

either from activation of endogenous mechanisms known to be generators of oxygenated free radicals, such as the energetic metabolism at the level of the respiratory chains or the activity of the macrophages particularly stimulated in the case of inflammation, or from genesis induced by exogenous factors such as electromagnetic waves (ionising or non-ionising radiation) or hyper-oxygenation.

Among the mechanisms induced by excessive production of oxygenated free radicals, scientists are in agreement in considering that the most important is lipoperoxidation which corresponds to the degradation under the effect of radical reactions of the polyunsaturated fatty acids present in the phospholipids constituting the membranes of living cells; as a consequence, these molecular species are the privileged target of the radical attacks.

It has been possible to determine experimentally that under the effect of oxygenated free radicals, the molecules of polyunsaturated fatty acid tend to oxidise and to generate numerous degradation products, among which the most important are aldehydes, especially malondialdehyde. The consequence of this catabolism is a loss of the integrity and the stability of the polyunsaturated fatty acids, which manifests itself in a profound change in the cellular integrity.

It is generally accepted that these phenomena are involved in pathologies ass varied as rheumatoid polyarthritis, certain cancers, certain neuro-degenerative diseases (Alzheimers's, Parkinson's), cerebral and cardiac ischemias and, in general terms, ageing and cell death.

Besides the above-mentioned classic protective systems (SOD, catalase, vitamin E, . . .), it has been known for several years that certain flavonoids of vegetable origin are excellent at trapping free radicals. It has been possible to ascertain that in this group the most interesting appear to be the procyanidols or proanthocyanidines which correspond to hydrolysable tannins constituted by a glucidic molecule on which is esterified gallic acid or one of its derivatives and which are capable of liberating cyanidol by hydrolysis in an acid medium.

According to their degree of increasing polymerisation, the procyanidols are characterised by the following terms: monomers, dimers, trimers, tetramers, oligomers and condensates; among the monomers, the most common are epigallocatechin and epigallocatechin gallate. It has in fact been found that these compounds have a very high intrinsic efficacy and in particular are markedly more active than vitamin E.

Starting from this general knowledge, there has already been proposed, according to the publication JP-A-04/164 030, a prophylactic composition for protection against disorders linked to radioactivity—such as may occur for example in patients who are treated with radio-therapy, or in permanent operators of apparatus emitting radioactive radiation—capable of being absorbed orally and the active constituents of which are previously purified epigallocatechin or epigallocatechin gallate monomers. This Japanese publication indicates that this prophylactic composition may be constituted by a mixture of epigallocatechin and epigallocatechin gallate in a ratio of ⅓ obtained from leaves of green tea.

The preparation of this composition, however, has the drawback of requiring extraction and purification operations which are long and expensive, and therefore particularly inconvenient.

According to the invention, the idea was conceived of remedying these drawbacks by the use, for preparing an absorbable prophylactic composition providing protection against ionising or non-ionising radiation, not of a composition based on previously isolated constituents but of a crude extract of the residual fractions of crushed grapes, that is to say, of a product available in large quantities and therefore not difficult to obtain.

According to the invention, such a crude extract may contain pips and/or stalks and/or skins. It may also be obtained from residual press cakes from the manufacture of grapeseed oil.

It should be noted that in the course of wine-making operation the bunches of grapes are squashed, that is to say, partially crushed in order to liberate the must which contains approximately 80% juice and 20% solid matter essentially constituted by the pips, stalks and skins. This must is then transferred to a fermentation vat in which occur the different chemical reactions of maceration and fermentation which permit the transformation of the grape into wine. In the course of these reactions, part of the constituents initially contained in the solid matter diffuses into the juice. The residual solid matter is then separated from the juice then pressed so as to obtain a wine known as "press" wine, and a residue termed "marc".

This residue may be distilled to produce brandy, or be used for animal feed.

Another outlet for more or less dried wine-making marcs corresponds to the manufacture of grapeseed oil by a pressing operation during the course of which the fatty part is separated from a press cake.

It should be noted that it has already been proposed to use by-products or wine-making for the preparation, after purification, of a medicament intended for the treatment of venous circulation problems: Endotelon®.

In spite of the various possibilities mentioned above, the major part of the wine-making marcs and of the press cakes from the manufacture of grapeseed oil is at present poorly exploited.

However, different earlier studies have made it possible to demonstrate that the grape pips present in these residues are particularly rich in procyanidols and contain, in particular, large amounts of epigallocatechin and epigallocatechin gallate which can be found in monomer form but also in dimer, trimer and oligomer form.

According to the invention, it has been ascertained that these procyanidols are also at least partially present in the above-mentioned by-products of wine-making, besides other constituents such as catechin, or even gallic acid or caffeic acid.

It has consequently been proposed to use a crude extract of all or parts of the residual fraction of crushed grapes for preparing an absorbable prophylactic composition providing protection against ionising or non-ionising electromagnetic waves.

It has been found that such a crude extract, surprisingly, has a markedly greater efficacy than that which epigallocatechin and epigallocatechin gallate which are isolated, or even associated with each other, have on the prevention of lipidic changes induced by radiation.

Taking into account the foregoing, the use according to the invention has the advantage of making it possible to derive value from the by-products of wine-making vines.

The invention also relates to an absorbable prophylactic composition providing protection against ionising or non-ionising electromagnetic waves.

According to the invention, this prophylactic composition is characterised in that it is constituted by a crude extract of all or parts of the residual fractions of crushed grapes containing essentially catechin, epicatechin and gallic acid, the catechin and epicatechin being able either to be associated with gallic acid or to be in a non-galloylated form, and these compounds being in the form of monomers or in the form of homogeneous or heterogeneous oligomers having different degrees of polymerisation, and in that it contains 10 to 30% of monomers, 10 to 30% of dimers, 10 to 30% of trimers and 30 to 60% of tetramers.

According to another characteristic of the invention, the composition contains traces of caffeic acid.

By way of a non-limiting example, such a crude extract may be obtained by a process which is known per se, in which:

a preparation based on grape pips is pulverized,
 the powder thus obtained is subjected to a first extraction with acetone,
 the extract thus obtained is separated by filtration,
 sodium chloride is added to it to saturation point,
 the acetone is evaporated,
 the extract is taken up again with distilled water,
 the solution thus obtained is subjected to a second extraction with ethyl acetate,
 the organic phase is separated out and this is subjected to lyophilisation so as to obtain the crude extract.

It should be noted that it is of advantage to carry out the pulverisation of the base preparation in the presence of dry ice in order to make it easier and to obtain greater homogenity.

It should also be noted that this base preparation is as a general rule relatively rich in apolar compounds which it is advisable to eliminate in order to obtain a satisfaction composition at the end of the process.

To this end, it is of advantage to subject the solution to intermediate extraction with diethyl ether before carrying out the second extraction.

A base preparation of grape pips of Bordeaux origin was treated, by way of example, by the above-mentioned process, using 70% acetone for the first extraction.

After lyophilisation, a composition was thus obtained containing 34% of catechin, 36% of epicatechin, 11.6% of gallic acid and 0.007% of caffeic acid.

It was also found that this composition contained 19% of monomers, 18% of dimers, 21% of trimers and 42% of tetramers.

Taking into account its good intestinal absorption and its rapid diffusion in the organism, the daily dose "per os" of the above-mentioned crude extract represents a regular nutritional supplement making it possible to combat the production of oxygenated free radicals induced by the action of radiation or oxydating stress exceeding the endogenous capacities for protection.

With regard to the recommendations for use, the quantity of extract to be ingested may vary from case to case, but it is desirable as a general rule to use daily doses of 20 mg to 3 g for an adult male.

The lower limit of this range applies by way of example to persons regularly exposed to weak radiation, while the upper limit is more especially suited to persons subjected to intense irradiation of short duration.

Different tests have made it possible to demonstrate the efficacy of the crude extract according to the invention against changes induced by ionising radiation (X-rays) and non-ionising radiation (UV-C). The effficacy of this extract was first studied on pure polyunsaturated fatty acids in aqueous solution after induction of the oxydating stress by UV-C rays (200 $\mu W/cm^2$; 24 hrs). It was thus possible to obtain total protection of these molecules starting from 2 mg/l of extract in the medium.

A study was then made of the effect of this extract on the attacks induced by UV-C rays on the membranal lipids of the brain and the liver of mice. There again, proof was provided of the total efficacy of this extract starting from a concentration of 4 mg/l.

In a third step, a study was made of the effect of UV-C radiation and X-rays on human fibroblastic cells in culture and also the protection provided by the crude extract according to the invention. Observation of the cellular lysis after UV-C irradiation (200 $\mu W/cm^2$; 1 hr) showed that the protection provided by this extract for the cells in culture was dose-dependent and that it is greater than 50% for a concentration of extract of 40 mg/l.

For X-rays, the cellular viability was taken into consideration. This index was evaluated by cellular enumeration, but also by observing the power of proliferation of the cells placed in culture again after irradiation with X-rays (30 Grays at the rate of 2 Gy/min). This made it possible to ascertain that, starting from 20 mg/l of crude extract in the medium, the number of dead cells is significantly reduced. In addition, the proliferation of the cells which is blocked in the cells irradiated in the absence of extract is to a great extent restored in the cells irradiated in the presence of this extract.

Finally, a study was made of the effect of the extract according to the invention on the haematopoietic system after total irradiation of male rats with X-rays (5 Gy in 3 sessions). Previously, a series of rats were force-fed with 60 mg/day of extract. Six days after the last irradiation, the animals were anaesthetized and the blood was sampled at the carotid. Blood analysis was carried out on each of the samples.

Before irradiation, no toxic effect was observed in the animals having ingested the preparation according to the invention.

The results of this experiment showed that there was a reduction in all the blood constituents and parameters (red blood cells, platelets, haematocrits, haemoglobin, polyneutrophiles, lymphocytes and monocytes) in the rats irradiated without pre-treatment, and that there was a marked improvement in the animals previously force-fed with the crude extract according to the invention.

By way of example, a platelet count was carried out on control animals, irradiated animals and irradiated animals previously treated with the extract according to the invention. The following results were thus obtained:

| control animals | 327.5 ± 103.5 G/l |
| irradiated animals | 152.66 ± 49.93 G/l |
| animals treated then irradiated | 277.66 ± 78.54 G/l |

These results clearly show the efficacy in vivo of the extract according to the invention.

In order to highlight the superiority of the crude extract according to the invention compared with isolated epigallocatechin and epigallocatechin gallate, according to the publication JP-A-04/164 030, a preparation of microsomes of baboon liver was irradiated with UV-C (200 $\mu$W/cm$^2$) for 15 hours in the presence of epigallocatechin (EGC), of epigallocatechin gallate (EGCG) or of the crude extract according to the invention (I).

The additions were made in such a way as always to have the same quantity of epicatechin, that is to say, 1.45 mg/l.

The residual polyunsaturated fatty acids (AGPI) (20:4 n–6 and 22:6 n–3) were then quantified and also malondialdehyde (MDA) which is a product of their degradation.

This test allowed the following results to be obtained:

| Concentration | MDA ($\mu$M) | AGPI | |
| --- | --- | --- | --- |
| | | 20:4 n – 6 ($\mu$g/ml) | 22:6 n – 3 ($\mu$g/ml) |
| Non-irradiated controls | 0 | 137.85 ± 2.65 | 42.43 ± 14.0 |
| Samples irradiated without additive | 34.17 ± 4.07 | 081.73 ± 7.65 | 15.40 ± 1.57 |
| Samples irradiated + I | 22.66 ± 1.75 | 136.29 ± 0.08 | 45.25 ± 9.61 |
| Samples irradiated + EGC | 32.02 ± 2.60 | 094.53 ± 9.11 | 24.05 ± 2.36 |
| Samples irradiated + EGCG | 32.25 ± 0.76 | 098.59 ± 21 | 31.40 ± 1.48 |

These results prove that irradiation of the microsomes results in degradation of the polyunsaturated fatty acids and an increase in the production of malondialdehyde.

The extract according to the invention appears to provide significant protection for the microsomes against these changes, which is not the case with isolated epigallocatechin and epigallocatechin gallate.

The same test was then repeated, irradiating a preparation of microsomes of baboon liver at a lower proteic concentration in the presence of the crude extract of grape pips according to the invention and of a mixture consisting of ¼ epigallocatechin and ¾ epigallocatechin gallate.

The additions were once again carried out in such a way as to have 1.45 mg/l of epicatechin in all cases.

The analyses carried out, similar to the above-mentioned test, allowed the following results to be obtained:

| Concentration | MDA ($\mu$M) | AGPI | |
| --- | --- | --- | --- |
| | | 20:4 n – 6 ($\mu$g/ml) | 22:6 n – 3 ($\mu$g/ml |
| Non-irradiated controls | 0.378 ± 0.05 | 18.96 ± 0.86 | 8.21 ± 1.85 |
| Samples irradiated without additive | 14.93 ± 0.35 | 6.66 ± 0.11 | undetectable |
| Samples irradiated + I | 5.91 ± 1.76 | 16.59 ± 0.01 | 7.51 ± 0.47 |
| Samples irradiated + EGC/EGCG mixture | 14.186 ± 0.37 | 09.59 ± 1.15 | 2.95 ± 0.99 |

This text again made it possible to prove that the extract according to the invention allows protection of the microsomes against the changes induced by UV-C rays, while the epigallocatechin/epigallocatechin gallate mixture appears totally ineffective at the doses used.

What is claimed is:

1. A method of making absorbable prophylactic composition from solid material comprising a crude extract derived from the pips, stalks, and/or skins and/or combinations thereof from crushed grapes, and/or residual press cakes from the manufacture of grapeseed oil and/or combinations thereof for protection against ionizing or nonionizing radiation, said method comprising:
   a) pulverizing said solid material to form powdered material;
   b) subjecting the powdered material to a first extraction with acetone to provide an extract;
   c) separating the extract;
   d) adding sodium chloride to the extract;
   e) evaporating the acetone from the extract;
   f) mixing the extract with water to form a solution;
   g) subjecting the solution to a second extraction with ethyl acetate to obtain an organic phase;
   h) separating the organic phase and subjecting the organic phase to lyophilisation to provide said prophylactic composition.

2. The method of claim 1, wherein the solid material extracted from the grapes comprises pips, stalks, skins, or combinations thereof.

3. The method as recited in claim 1, wherein the material extracted from grapes comprises pips.

4. The method as recited in claim 1, wherein the material extracted from grapes is subjected to extraction with diethyl ether before the second extraction.

5. The method as recited in claim 4, wherein subjecting the material to extraction with diethyl ether is accomplished prior to subjecting the solution to the extraction with ethyl acetate.

6. The method as recited in claim 1, further comprising pulverizing the solid material extracted from grapes in the presence of a freezing medium.

7. The method as recited in claim 6, wherein said freezing medium comprises dry ice.

8. An absorbable prophylactic composition made in accordance with a method recited in claim 1.

9. The composition as recited in claim 8, wherein said composition is derived from solid material extracted from grapes which contains catechin, epicatechin and gallic acid, the catechin and epicatechin being able to be intermixed with the gallic acid or to be in a nongalloylated form.

10. The composition as recited in claim 9, wherein the catechin, epicatechin and gallic acid are in the form of monomers in the form homogeneous or heterogeneous oligomers having different degrees of polymerization.

11. The composition as recited in claim 8, wherein the solid material extracted from grapes contains 10% to 30% monomers, 10 to 30% dimers, 10 to 30% of trimers, and 30 to 60% tetramers.

12. The composition as recited in claim 11, wherein the solid material extracted from grapes contains traces of caffeic acid.

13. A prophylactic composition for protection against ionizing or nonionizing radiation, which comprises a crude extract derived from the pips, stalks, and/or skins and/or combinations thereof from crushed grapes, and/or residual press cakes from the manufacture of grapeseed oil and/or combinations thereof, comprising catechin, epicatechin and gallic acid, the catechin and epicatechin being able either to be intermixed with gallic acid or to be in nongalloviated form.

14. The composition as recited in claim 13 wherein the catechin and epicatechin and gallic acid is in the form of monomers or in the form of homogeneous or heterogeneous oligomers.

15. The composition as recited in claim 14, wherein the composition contains 10 to 30% of monomers, 10 to 30% dimers, 10 to 30% of trimers, and 30 to 60% tetramers.

16. A method of providing protection against ionizing or nonionizing radiation by ingesting a therapeutic dose of a composition derived from pips, stalks, and/or skins from crushed grapes and/or combinations thereof, and/or residual press cakes from the manufacture of grapeseed oil wherein said composition comprises a solid material extracted from grapes which contains catechin, epicatechin and gallic acid, the catechin and epicatechin being able to be intermixed with the gallic acid or to be in a nongalloylated form.

17. The method as recited in claim 16, wherein the catechin, epicatechin and gallic acid are in the form of monomers in the form of homogeneous or heterogeneous oligomers.

18. The method as recited in claim 17, wherein said composition contains 10% to 30% monomers, 10 to 30% dimers, 10 to 30% of trimers, and 30 to 60% tetramers.

19. The method as recited in claim 18, wherein said composition comprises the solid material extracted from grapes contains traces of caffeic acid.

* * * * *